US006340593B1

(12) United States Patent
Cardineau et al.

(10) Patent No.: US 6,340,593 B1
(45) Date of Patent: Jan. 22, 2002

(54) PLANT-OPTIMIZED POLYNUCLEOTIDES ENCODING APPROXIMATELY 15 KDA AND APPROXIMATELY 45 KDA PESTICIDAL PROTEINS

(75) Inventors: Guy A. Cardineau, Poway; Steven J. Stelman; Kenneth E. Narva, both of San Diego, all of CA (US)

(73) Assignee: Mycogen Corporation, Indianapolis, IN (US)

( * ) Notice: Subject to any disclaimer, the term of this patent is extended or adjusted under 35 U.S.C. 154(b) by 0 days.

(21) Appl. No.: 09/422,487

(22) Filed: Oct. 21, 1999

Related U.S. Application Data

(60) Provisional application No. 60/105,408, filed on Oct. 23, 1998, and provisional application No. 60/105,359, filed on Oct. 23, 1998.

(51) Int. Cl.[7] .............................. C12N 1/21; C12N 5/14; C12N 15/32; C12N 15/82
(52) U.S. Cl. .................... 435/412; 435/252.3; 435/419; 435/468; 435/471; 536/23.71
(58) Field of Search ...................... 536/23.71; 435/69.1, 435/252.3, 419, 468, 471; 800/279, 302

(56) References Cited

U.S. PATENT DOCUMENTS

| 5,380,831 A | 1/1995 | Adang et al. ............ 536/23.71 |
| 5,567,862 A | 10/1996 | Adang et al. ............... 800/205 |

FOREIGN PATENT DOCUMENTS

| EP | 0359472 | 9/1989 |
| WO | 9307278 | 4/1993 |
| WO | 9534656 | 12/1995 |
| WO | 9713402 | 4/1997 |
| WO | 9740162 | 10/1997 |

OTHER PUBLICATIONS

Koziel, M. G. et al., "Optimizing expression of transgenes with an emphasis on post–transcriptional events." 1996, Plant Molecular Biology, vol. 32, pp. 393–405.*

Ely, S. (1993), "The Engineering of Plants to Express *Bacillus thuringiensis* δ–Endotoxins," *Bacillus thuringiensis, An Environmental Biopesticide: Theory and Practice*, Entwistle et al., Ed. (1993, John Wiley & Sons, Ltd.).

Hofte et al. (1989), "Insecticidal Crystal Proteins of *Bacillus thuringiensis*," *Microbiological Reviews* 53(2):242–255.

Crickmore et al. (1996), Society for Invertebrate Pathology, 29th Annual Meeting, 3rd International Colloquium on *Bacillus thuringiensis*, University of Cordoba, Cordoba, Spain, Sep. 1–6, abstract.

Murray et al. (1989), "Codon Usage in Plant Genes," *Nucleic Acids Research* 17(2):477–498.

Fujimoto et al. (1993), "Insect Resistant Rice Generated by Introduction of a Modified δ–endotoxin Gene of *Bacillus thuringiensis*," *Bio/Technology* 11:1151–1155.

* cited by examiner

*Primary Examiner*—Amy J. Nelson
(74) *Attorney, Agent, or Firm*—Saliwanchik, Lloyd & Saliwanchik

(57) ABSTRACT

The subject invention provides new, plant-optimized polynucleotide sequences that encode pesticidal toxins. The polynucleotide sequences of the subject invention have certain modifications, compared to wild-type sequences, for example, that make them particularly well-suited for optimized expression in plants. Using the polynucleotide sequences described herein, the transformation of plants can be accomplished, using techniques known to those skilled in the art, in order to confer pest resistance upon the plants. In preferred embodiments, the subject invention provides plant-optimized polynucleotide sequences which encode approximately 15 kDa and approximately 45 kDa pesticidal proteins.

11 Claims, No Drawings

PLANT-OPTIMIZED POLYNUCLEOTIDES ENCODING APPROXIMATELY 15 KDA AND APPROXIMATELY 45 KDA PESTICIDAL PROTEINS

CROSS-REFERENCE TO RELATED APPLICATIONS

The subject application claims priority to Ser. No. 60/105,408 and Ser. No. 60/105,359, each filed on Oct. 23, 1998.

BACKGROUND OF THE INVENTION

Insects and other pests cost farmers billions of dollars annually in crop losses and in the expense of keeping these pests under control. The losses caused by insect pests in agricultural production environments include decrease in crop yield, reduced crop quality, and increased harvesting costs.

Chemical pesticides have provided an effective method of pest control; however, the public has become concerned about the amount of residual chemicals which might be found in food, ground water, and the environment. Therefore, synthetic chemical pesticides are being increasingly scrutinized, and correctly so, for their potential toxic environmental consequences. Synthetic chemical pesticides can poison the soil and underlying aquifers, pollute surface waters as a result of runoff, and destroy non-target life forms. Synthetic chemical control agents have the further disadvantage of presenting public safety hazards when they are applied in areas where pets, farm animals, or children may come into contact with them. They may also provide health hazards to applicants, especially if the proper application techniques are not followed. Regulatory agencies around the world are restricting and/or banning the uses of many pesticides and particularly the synthetic chemical pesticides which are persistent in the environment and enter the food chain. Examples of widely used synthetic chemical pesticides include the organochlorines, e.g., DDT, mirex, kepone, lindane, aldrin, chlordane, aldicarb, and dieldrin; the organophosphates, e.g., chlorpyrifos, parathion, malathion, and diazinon; and carbamates. Stringent new restrictions on the use of pesticides and the elimination of some effective pesticides from the market place could limit economical and effective options for controlling costly pests.

Because of the problems associated with the use of synthetic chemical pesticides, there exists a clear need to limit the use of these agents and a need to identify alternative control agents. The replacement of synthetic chemical pesticides, or combination of these agents with biological pesticides, could reduce the levels of toxic chemicals in the environment.

A biological pesticidal agent that is being used with increasing popularity is the soil microbe *Bacillus thuringiensis* (B.t.). The soil microbe *Bacillus thuringiensis* (B.t.) is a Gram-positive, spore-forming bacterium. Most strains of B.t. do not exhibit pesticidal activity. Some B.t. strains produce, and can be characterized by, paraspiral crystalline protein inclusions. These "δ-endotoxins," which typically have specific pesticidal activity, are different from exotoxins, which have a non-specific host range. These inclusions often appear microscopically as distinctively shaped crystals. The proteins can be highly toxic to pests and are specific in their toxic activity.

Preparations of the spores and crystals of *B. thuringietisis* subsp. kurstaki have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

The cloning and expression of a B.t. crystal protein gene in *Escherichia coli* was described in the published literature more than 15 years ago (Schnepf, H. E., H. R. Whiteley [1981] *Proc. Natl. Acad. Sci. USA* 78:2893–2897.). U.S. Pat. No. 4,448,885 and U.S. Pat. No. 4,467,036 both disclose the expression of B.t. crystal protein in *E. coli*. Recombinant DNA-based B.t. products have been produced and approved for use.

Commercial use of B.t. pesticides was originally restricted to a narrow range of lepidopteran (caterpillar) pests. More recently, however, investigators have discovered B.t. pesticides with specificities for a much broader range of pests. For example, other species of B.t., namely *israelensis* and *morrisoni* (a.k.a. *tenebrionis*, a.k.a. B.t. M-7), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255).

New subspecies of B.t. have now been identified, and genes responsible for active δ-endotoxin proteins have been isolated and sequenced (Höfte, H., H. R. Whiteley [1989] *Microbiological Reviews* 52(2):242–255). Höfte and Whiteley classified B.t. crystal protein genes into four major classes. The classes were cryI (Lepidoptera-specific), cryII (Lepidoptera- and Diptera-specific), cryIII (Coleoptera-specific), and cryIV (Diptera-specific). The discovery of strains specifically toxic to other pests has been reported (Feitelson, J. S., J. Payne, L. Kim [1992] *Bio/Technology* 10:271–275). For example, the designations CryV and CryVI have been proposed for two new groups of nematode-active toxins.

The 1989 nomenclature and classification scheme of Höfte and Whiteley was based on both the deduced amino acid sequence and the host range of the toxin. That system was adapted to cover 14 different types of toxin genes which were divided into five major classes. The number of sequenced *Bacillus thuringiensis* crystal protein genes currently stands at more than 50. A revised nomenclature scheme has been proposed which is based solely on amino acid identity (Crickmore et al. [1996] Society for Invertebrate Pathology, 29th Annual Meeting, IIIrd International Colloquium on *Bacillus thiuringiensis*, University of Cordoba, Cordoba, Spain, Sep. 1–6, 1996, abstract). The mnemonic "cry" has been retained for all of the toxin genes except cytA and cytB, which remain a separate class. Roman numerals have been exchanged for Arabic numerals in the primary rank, and the parentheses in the tertiary rank have been removed. Many of the original names have been retained, although a number have been reclassified.

With the use of genetic engineering techniques, new approaches for delivering B.t. toxins to agricultural environments are under development, including the use of plants genetically engineered with B.t. toxin genes for insect resistance and the use of stabilized, microbial cells as delivery vehicles of B.t. toxins (Gaertner, F. H., L. Kim [1988] *TIBTECH* 6:S4–S7). Thus, isolated B.t. endotoxin genes are becoming commercially valuable.

Various improvements have been achieved by modifying B.t. toxins and/or their genes. For example, U.S. Pat. Nos. 5,380,831 and 5,567,862 relate to the production of synthetic insecticidal crystal protein genes having improved expression in plants.

Obstacles to the successful agricultural use of B.t. toxins include the development of resistance to B.t. toxins by insects. In addition, certain insects can be refractory to the effects of B.t. The latter includes insects such as boll weevil and black cutworm as well as adult insects of most species which heretofore have demonstrated no apparent significant sensitivity to B.t. δ-endotoxins.

Thus, resistance management strategies in B.t. plant technology have become of great interest, and there remains a great need for new toxin genes. For example, WO 97/40162 (published PCT application) discloses 15 kDa and 45 kDa coleopteran-active proteins obtainable from B.t. isolates PS80JJ1 and PS149B1.

As a result of extensive research and resource investment, patents continue to issue for new B.t. isolates, toxins, and genes, and for new uses of B.t. isolates. See Feitelson et al., supra, for a review. U.S. Pat. No. 5,589,382 discloses B.t. isolate PS80JJ1 as having activity against nematodes. U.S. Pat. No. 5,632,987 discloses B.t. isolate PS80JJ1 as having activity against corn rootworm. However, the discovery of new B.t. isolates and new uses of known B.t. isolates remains an empirical, unpredictable art.

There remains a great need for new toxin genes that can be successfully expressed at adequate levels in plants in a manner that will result in the effective control of insects and other pests.

BRIEF SUMMARY OF THE INVENTION

The subject invention concerns materials and methods useful in the control of pests and, particularly, plant pests. More specifically, the subject invention provides new, plant-optimized polynucleotide sequences that encode pesticidal proteins. The polynucleotide sequences of the subject invention have certain modifications, compared to wild-type sequences, that make them particularly well-suited for optimized expression in plants. Using the polynucleotide sequences described herein, the transformation of plants can be accomplished, using techniques known to those skilled in the art, in order to confer pest resistance upon said plants. In a preferred embodiment, the subject invention provides plant-optimized polynucleotide sequences which encode approximately 15 kDa and approximately 45 kDa pesticidal proteins.

DESCRIPTION OF THE SEQUENCES

SEQ ID NO. 1 is a polynucleotide sequence for a gene designated 80JJ1-15-PO5, which is optimized for expression in maize. This gene encodes an approximately 15 kDa protein. This gene and protein were disclosed in WO 97/40162.

SEQ ID NO. 2 is a novel polynucleotide sequence for a gene designated 80JJ1-15-PO7, which is optimized for expression in maize. This is an alternative gene that encodes an approximately 15 kDa protein.

SEQ ID NO. 3 is an amino acid sequence for a novel pesticidally active protein encoded by the gene designated 80JJ1-15-PO7.

SEQ ID NO. 4 is a polynucleotide sequence for a gene designated 80JJ1-45-PO, which is optimized for expression in maize. This gene encodes an approximately 45 kDa protein. This gene was disclosed in WO 97/40162.

SEQ ID NO. 5 is a novel polynucleotide sequence for a gene designated 149B1-15-PO, which is optimized for expression in Zea mays. This gene encodes an approximately 15 kDa protein obtainable from PS149B1 that is disclosed in WO 97/40162.

SEQ ID NO. 6 is a novel polynucleotide sequence for a gene designated 149B1-45-PO, which is optimized for expression in Zea mays. This gene encodes an approximately 45 kDa protein obtainable from PS149B1 that is disclosed in WO 97/40162.

DETAILED DISCLOSURE OF THE INVENTION

The subject invention concerns materials and methods useful in the control of pests and, particularly, plant pests. More specifically, the subject invention provides new, plant-optimized polynucleotide sequences that encode pesticidal proteins. The polynucleotide sequences of the subject invention have certain modifications, compared to wild-type sequences, that make them particularly well-suited for optimized expression in plants. Using the polynucleotide sequences described herein, the transformation of plants can be accomplished, using techniques known to those skilled in the art, in order to confer pest resistance upon said plants. In a preferred embodiment, the subject invention provides plant-optimized polynucleotide sequences which encode approximately 15 kDa and approximately 45 kDa pesticidal proteins.

Using techniques such as computer- or software-assisted sequence alignments, differences can be noted in the nucleotide sequence of the subject plant-optimized genes as compared to the wild-type genes or to previously known genes. Similarly, differences in the unique amino acid sequences of the subject invention can be noted as compared to wild-type toxins or to previously known toxins.

It should be apparent to a person skilled in this art that, given the sequences of the genes as set forth herein, the genes of the subject invention can be obtained through several means. In preferred embodiments, the subject genes may be constructed synthetically by using a gene synthesizer, for example. The specific genes exemplified herein can also be obtained by modifying, according to the teachings of the subject invention, certain wild-type genes (for example, by point-mutation techniques) from certain isolates deposited at a culture depository as discussed below.

Certain cultures discussed in this application have been deposited in the Agricultural Research Service Pat. Culture Collection (NRRL), Northern Regional Research Center, 1815 North University Street, Peoria, Ill. 61604, USA. The deposited strains listed below are disclosed in the patent references as discussed above in the section entitled "Background of the Invention."

| Subculture | Accession Number | Deposit Date |
| --- | --- | --- |
| B.T. PS80JJ1 | NRRL B-18679 | July 17, 1990 |
| E. coli (NM522) (pMYC2421) (PS80JJ1 14 kDa & 45 kDa) | NRRL B-21555 | March 28, 1996 |
| E. coli (NM522) (pMYC2426) (PS80JJ1 14 kDa & 45 kDa) | NRRL B-21671 | March 26, 1997 |
| B.t. PS149B1 | NRRL B-21553 | March 28, 1996 |
| E. coli (NM522) (pMYC2429) (PS149B1 15 kDa & 45 kDa) | NRRL B-21673 | March 26, 1997 |

It should be understood that the availability of a deposit does not constitute a license to practice the subject invention in derogation of patent rights granted by governmental action.

Genes and toxins. The subject invention includes, in preferred embodiments, polynucleotide sequences optimized for expression in plants, wherein said sequences are selected from the group consisting of SEQ ID NO. 2, SEQ ID NO. 5, and SEQ ID NO. 6. SEQ ID NO. 2 encodes a preferred protein that is shown in SEQ ID NO. 3.

The polynucleotides of the subject invention can be used to form complete "genes" to encode proteins or peptides in a desired host cell. For example, as the skilled artisan would readily recognize, SEQ ID NO. 2, SEQ ID NO. 5, and SEQ ID NO. 6 are shown without stop codons. SEQ ID NO. 2, SEQ ID NO. 5, and/or SEQ ID NO. 6 can be appropriately placed under the control of a promoter in a host of interest, as is readily known in the art.

As the skilled artisan would readily recognize, DNA can exist in a double-stranded form. In this arrangement, one strand is complementary to the other strand and vice versa. The "coding strand" is often used in the art to refer to the strand having a series of codons (a codon is three nucleotides that can be read three-at-a-time to yield a particular amino acid) that can be read as an open reading frame (ORF) to form a protein or peptide of interest. In order to express a protein in vivo, a strand of DNA is typically translated into a complementary strand of RNA which is used as the template for the protein. As DNA is replicated in a plant (for example) additional, complementary strands of DNA are produced. Thus, the subject invention includes the use of either the exemplified polynucleotides shown in the attached sequence listing or the complementary strands. RNA and PNA (peptide nucleic acids) that are functionally equivalent to the specifically exemplified, novel DNA molecules are included in the subject invention.

Certain DNA sequences of the subject invention have been specifically exemplified herein. These sequences are exemplary of the subject invention. It should be readily apparent that the subject invention includes not only the genes and sequences specifically exemplified herein but also equivalents and variants thereof (such as mutants, fusions, chimerics, truncations, fragments, and smaller genes) that exhibit the same or similar characteristics relating to expressing toxins in plants, as compared to those specifically disclosed herein. As used herein, "variants" and "equivalents" refer to sequences which have nucleotide (or amino acid) substitutions, deletions (internal and/or terminal), additions, or insertions which do not materially affect the expression of the subject genes, and the resultant pesticidal activity, in plants. Fragments of polynucleotide proteins retaining pesticidal activity, and "pesticidal portions" of full-length proteins, are also included in this definition.

Genes can be modified, and variations of genes may be readily constructed, using standard techniques. For example, techniques for making point mutations are well known in the art. In addition, commercially available exonucleases or endonucleases can be used according to standard procedures, and enzymes such as Bal31 or site-directed mutagenesis can be used to systematically cut off nucleotides from the ends of these genes. Useful genes can also be obtained using a variety of restriction enzymes.

It should be noted that equivalent genes will encode toxins that have high amino acid identity or homology with the toxins encoded by the subject genes. The amino acid homology will be highest in critical regions of the toxin which account for biological activity or are involved in the determination of three-dimensional configuration which ultimately is responsible for the biological activity. In this regard, certain substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table I provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the ability of plants to express the subject DNA sequences or from the biological activity of the toxin.

As used herein, reference to "isolated" polynucleotides and/or "purified" toxins refers to these molecules when they are not associated with the other molecules with which they would be found in nature and would include their use in plants. Thus, reference to "isolated" and/or "purified" signifies the involvement of the "hand of man" as described herein.

Recombinant hosts. The toxin-encoding genes of the subject invention can be introduced into a wide variety of microbial or plant hosts. In some embodiments of the subject invention, transformed microbial hosts can be used in preliminary steps for preparing precursors, for example, that will eventually be used to transform, in preferred embodiments, plant cells and plants so that they express the toxins encoded by the genes of the subject invention. Microbes transformed and used in this manner are within the scope of the subject invention. Recombinant microbes may be, for example, a B.t., *E. coli*, or Pseudomnonas. Transformations can be made by those skilled in the art using standard techniques. Materials necessary for these transformations are disclosed herein or are otherwise readily available to the skilled artisan.

Thus, in preferred embodiments, expression of a gene of this invention results, directly or indirectly, in the intracellular production and maintenance of the protein of interest. When transformed plants are ingested by the pest, the pests will ingest the toxin. The result is a control of the pest.

The B.t. toxin gene can be introduced via a suitable vector into a host, preferably a plant host. There are many crops of interest, such as corn, wheat, rice, cotton, soybeans, and sunflowers. The genes of the subject invention arc particularly well suited for providing stable maintenance and expression, in the transformed plant, of the gene expressing the polypeptide pesticide, and, desirably, provide for improved protection of the pesticide from environmental degradation and inactivation.

Thus, the subject invention includes recombinant hosts comprising a polynucleotide sequence optimized for expression in a plant, wherein said sequence is selected from the group consisting of SEQ ID NO. 2, SEQ ID NO. 5, and SEQ ID NO. 6. The recombinant host can be, for example, a plant cell. Entire plants comprising the subject polynucleotides are also within the scope of the subject invention. In particularly preferred embodiments, a plant can be made resistant to corn rootworm damage by being transformed to express a polynucleotide, such as SEQ ID NO. 2, that encodes an approximately 15 kDa protein, together with a second polynucleotide, such as SEQ ID NO. 4, which encodes a 45 kDa protein. Likewise, SEQ ID NO. 5 and SEQ ID NO. 6 can be used together, under one promoter or separate promoters, such as the ubiquitin promoter. For that matter, the polynucleotide of SEQ ID NO. 2 and SEQ ID NO. 6 can be used together, or SEQ ID NO. 4 and SEQ ID NO. 5 can be used, for example.

While the subject invention provides specific embodiments of synthetic genes, other genes that are functionally equivalent to the genes exemplified herein can also be used to transform hosts, preferably plant hosts. Additional guidance for the production of synthetic genes can be found in, for example, U.S. Pat. No. 5,380,831.

All of the publications and patent references referred to or cited herein are hereby incorporated by reference in their entirety to the extent that they are not inconsistent with the explicit teachings of this specification.

Following is an example which illustrates procedures for practicing the invention. This example should not be construed as limiting.

EXAMPLE 1

Insertion of Toxin Genes Into Plants

One aspect of the subject invention is the transformation of plants with the subject polynucleotide sequences encoding insecticidal toxins. The transformed plants are resistant to attack by the target pest. The genes of the subject invention are optimized for use in plants.

Obviously, a promoter region capable of expressing the gene in a plant is needed. Thus, for in planta expression, the DNA of the subject invention is under the control of an appropriate promoter region. Techniques for obtaining in planta expression by using such constructs is known in the art. A preferred promoter region used for expression of both 15 kDa and 45 kDa transgenes is the *Zea mays* ubiquitin promoter plus *Z. mays* exon 1 and *Z. mays* intron I (Christensen, A. H., et al. 1992 Plant Mol. Biol. 18:675–689). A preferred transcriptional terminator for both transgenes is the potato proteinase inhibitor II (PinII) terminator (An, G. et al. 1989 Plant Cell 1:115–22).

Genes encoding pesticidal toxins, as disclosed herein, can be inserted into plant cells using a variety of techniques which are well known in the art. For example, in preferred embodiments, maize plants containing 14 kDa and 44 kDa transgenes were obtained by microprojectile bombardment using the Biolistics® Ò PDS-100He particle gun manufactured by Bio-Rad, essentially as described by Klein et al. (1987).

A large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordinly, the sequence encoding the B.t. toxin can be inserted into the vector at a suitable restriction site. The resulting plasmid is used for transformation into *E. coli.* The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids.

Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and sufficiently described in EP 120 516; Hoekema (1985) In: *The Binary Plant Vector System,* Offset-durkkerij Kanters B. V., Alblasserdam, Chapter 5; Fraley et al., *Crit. Rev. Plant Sci.* 4:1–46; and An et al. (1985) EMBO J 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters etal. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

It should be understood that the examples and embodiments described herein are for illustrative purposes only and that various modifications or changes in light thereof will be suggested to persons skilled in the art and are to be included within the spirit and purview of this application and the following claims.

What is claimed is:

1. A modified polynucleotide comprising a nucleotide sequence selected from the group consisting of SEQ ID NO:5 and SEQ ID NO:6.

2. The polynucleotide according to claim 1 wherein said nucleotide sequence is SEQ ID NO:5.

3. The polynucleotide according to claim 1 wherein said nucleotide sequence is SEQ ID NO:6.

4. A cell that comprises a modified polynucleotide wherein said polynucleotide comprises a nucleotide sequence selected from the group consisting of SEQ ID NO:5 and SEQ ID NO:6, wherein said cell is a plant cell or a microbial cell.

5. The cell according to claim 4 wherein said nucleotide sequence is SEQ ID NO:5.

6. The cell according to claim 4 wherein said nucleotide sequence is SEQ ID NO:6.

7. The cell according to claim 4 wherein said cell is a plant cell.

8. The cell according to claim 7 wherein said plant cell is a maize cell.

9. A method if producing a cell wherein said method comprises introducing a modified polynucleotide into said cell, wherein said polynucleotide comprises a nucleotide sequence selected from the group consisting of SEQ ID NO:5 and SEQ ID NO:6, wherein said cell is a plant cell or a microbial cell.

10. The method according to claim 9 wherein said cell is a plant cell.

11. The method according to claim 10 wherein said plant cell is a maize cell.

* * * * *

UNITED STATES PATENT AND TRADEMARK OFFICE
CERTIFICATE OF CORRECTION

PATENT NO. : 6,340,593 B1
DATED : January 22, 2002
INVENTOR(S) : Guy A. Cardineau, Steven J. Stelman and Kenneth E. Narva It is certified that error appears in the above-identified patent and that said Letters Patent is hereby corrected as shown below:

Column 1,
Line 65, "*thuringietisis*" should read -- *thuringiensis* --.

Column 2,
Line 1, "HD- 1" should read -- HD-1 --.
Lines 37-38, "H
    öfte" should read -- Höfte --.
Line 47, "*thiuringiensis*" should read -- *thuringiensis* --.

Column 4,
Line 51, "B.T." should read -- B.t. --.

Column 6,
Line 36, "Pseudomnonas" should read -- Pseudomonas --.
Line 49, "arc" should read -- are --.

Column 7,
Line 34, "intron I" should read -- intron 1 --.
Line 52, "Accordinly," should read -- Accordingly, --.

Column 8,
Line 6, "EMBO J" should read -- EMBO J. --.
Line 38, "etal." should read -- et al. --.

Column 14,
Line 52, "if" should read -- of --.

Signed and Sealed this

Twenty-fourth Day of December, 2002

JAMES E. ROGAN
*Director of the United States Patent and Trademark Office*

SEQUENCE LISTING

<160> NUMBER OF SEQ ID NOS: 6

<210> SEQ ID NO 1
<211> LENGTH: 357
<212> TYPE: DNA
<213> ORGANISM: Artificial Sequence
<220> FEATURE:
<223> OTHER INFORMATION: Description of Artificial Sequence: Synthetic
      Bacillus thuringiensis toxin gene

<400> SEQUENCE: 1

```
atgtccgccc gcgaggtgca catcgagatc aacaacaaga cccgccacac cctccagctc      60
gaggacaaga ccaagctctc cggcggcagg tggcgcacct ccccgaccaa cgtggcccgc     120
gacaccatca agacgttcgt ggcggagtcc cacggcttca tgaccggcgt cgagggcatc     180
atctacttct ccgtgaacgg cgacgccgag atctccctcc acttcgacaa cccgtacatc     240
ggctccaaca agtgcgacgg ctcctccgac aagcccgagt acgaggtgat cacccagtcc     300
ggctccggcg acaagtccca cgtgacctac accatccaga ccgtgtccct ccgcctc        357
```

<210> SEQ ID NO 2
<211> LENGTH: 357
<212> TYPE: DNA
<213> ORGANISM: Artificial Sequence
<220> FEATURE:
<223> OTHER INFORMATION: Description of Artificial Sequence: Synthetic
      Bacillus thuringiensis toxin gene

<400> SEQUENCE: 2

```
atgtccgccc gcgaggtgca catcgagatc aacaacaaga cccgccacac cctccagctc      60
gaggacaaga ccaagctctc cggcggcagg tggcgcacct ccccgaccaa cgtggcccgc     120
gacaccatca agacgttcgt ggcggagtcc cacggcttca tgaccggcgt cgagggcatc     180
atctacttct ccgtgaacgg cgacgccgag atctccctcc acttcgacaa cccgtacatc     240
ggctccaaca agtccgacgg ctcctccgac aagcccgagt acgaggtgat cacccagtcc     300
ggctccggcg acaagtccca cgtgacctac accatccaga ccgtgtccct ccgcctc        357
```

<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Toxin
      encoded by synthetic Bacillus thuringiensis gene

<400> SEQUENCE: 3

```
Met Ser Ala Arg Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Val Glu Gly Ile Ile Tyr Phe Ser
     50                  55                  60

Val Asn Gly Asp Ala Glu Ile Ser Leu His Phe Asp Asn Pro Tyr Ile
 65                  70                  75                  80

Gly Ser Asn Lys Ser Asp Gly Ser Ser Asp Lys Pro Glu Tyr Glu Val
             85                  90                  95
```

```
Ile Thr Gln Ser Gly Ser Gly Asp Lys Ser His Val Thr Tyr Thr Ile
            100                 105                 110
Gln Thr Val Ser Leu Arg Leu
        115

<210> SEQ ID NO 4
<211> LENGTH: 1155
<212> TYPE: DNA
<213> ORGANISM: Artificial Sequence
<220> FEATURE:
<223> OTHER INFORMATION: Description of Artificial Sequence:  Synthetic
      Bacillus thuringiensis toxin gene

<400> SEQUENCE: 4
atgctcgaca  ccaacaaggt  gtacgagatc  tccaacctcg  ccaacggcct  ctacacctcc    60
acctacctct  ccctcgacga  ctccggcgtg  tccctcatgt  ccaagaagga  cgaggacatc   120
gacgactaca  acctcaagtg  gttcctcttc  ccgatcgaca  caaccagta   catcatcacc   180 tcctacggcg  ccaacaactg  caagtgtgg   aacgtgaaga  cgacaagat   caacgtgtcc   240 acctactcct  ccaccaactc  cgtgcagaag  tggcagatca  aggccaagga  ctcctcctac   300
atcatccagt  ccgacaacgg  caaggtgctc  accgcgggcg  tgggccagtc  cctcggcatc   360
gtgcgcctca  ccgacgagtt  cccggagaac  tccaaccagc  aatggaacct  caccccggtg   420
cagaccatcc  agctcccgca  gaagccgaag  atcgacgaga  agctcaagga  ccacccggag   480
tactccgaga  ccggcaacat  caaccccgaa  gccaccccgc  agctcatggg  ctggacccrc   540
gtgccgtgca  tcatggtgaa  cgactccaag  atcgacaaga  cacccagat   caagaccacc   600 ccgtactaca  tcttcaagaa  atacaagtac  tggaacctcg  ccaagggctc  caacgtgtcc   660
ctcctcccgc  accagaagcg  cagctacgac  tacgagtggg  gcaccgagaa  gaaccagaag   720
accaccatca  tcaacaccgt  gggcctgcag  atcaacatcg  actcggggat  gaagttcgag   780
gtgccggagg  tgggcggcgg  caccgaggac  atcaagaccc  agctcaccga  ggagctgaag   840
gtggagtact  ccaccgagac  caagatcatg  accaagtacc  aggagcactc  cgagatcgac   900
aacccgacca  ccagccgat   gaactccatc  ggcctcctca  tctacacctc  cctcgagctg   960
taccgctaca  acggcaccga  gatcaagatc  atggacatcg  agacctccga  ccacgacacc  1020
tacaccctca  cctcctaccc  gaaccacaag  gaggcgctgc  tgctgctgac  caaccactcc  1080
tacgaggagg  tggaggagat  caccaagatc  ccgaagcaca  ccctcatcaa  gctcaagaag  1140
cactacttca  agaag                                                       1155

<210> SEQ ID NO 5
<211> LENGTH: 369
<212> TYPE: DNA
<213> ORGANISM: Artificial Sequence
<220> FEATURE:
<223> OTHER INFORMATION: Description of Artificial Sequence:  Synthetic
      Bacillus thuringiensis toxin gene

<400> SEQUENCE: 5
atgtccgccc  gcgaggtgca  catcgacgtg  aacaacaaga  ccggccacac  cctccagctg    60
gaggacaaga  ccaagctcga  cggcggcagg  tggcgcacct  ccccgaccaa  cgtggccaac   120
gaccagatca  agaccttcgt  ggccgaatcc  aacggcttca  tgaccggcac  cgagggcacc   180
atctactact  ccatcaacgg  cgaggccgag  atcagcctct  acttcgacaa  cccgttcgcc   240
ggctccaaca  aatacgacgg  ccactccaac  aagtcccagt  acgagatcat  cacccagggc   300
ggctccggca  ccagtcccca  cgtgacctac  accatccaga  ccacctcctc  ccgctacggc   360
```

-continued

```
cacaagtcc                                                              369

<210> SEQ ID NO 6
<211> LENGTH: 1149
<212> TYPE: DNA
<213> ORGANISM: Artificial Sequence
<220> FEATURE:
<223> OTHER INFORMATION: Description of Artificial Sequence:  Synthetic
      Bacillus thuringiensis toxin gene

<400> SEQUENCE: 6
atgctcgaca ccaacaaggt gtacgagatc agcaaccacg ccaacggcct ctacgccgcc        60
acctacctct ccctcgacga ctccggcgtg tccctcatga acaagaacga cgacgacatc       120
gacgactaca acctcaagtg gttcctcttc ccgatcgacg acgaccagta catcatcacc       180
tcctacgccg ccaacaactg caaggtgtgg aacgtgaaca cgacaagat caacgtgtcc       240 acctactcct ccaccaactc catccagaag tggcagatca aggccaacgg ctcctcctac       300
gtgatccagt ccgacaacgg caaggtgctc accgccggca ccggccaggc cctcggcctc       360
atccgcctca ccgacgagtc ctccaacaac ccgaaccagc aatggaacct gacgtccgtg       420
cagaccatcc agctcccgca gaagccgatc atcgacacca agctcaagga ctacccgaag       480
tactccccga ccggcaacat cgacaacggc acctccccgc agctcatggg ctggaccctc       540
gtgccgtgca tcatggtgaa cgacccgaac atcgacaaga cacccagat caagaccacc       600 ccgtactaca tcctcaagaa gtaccagtac tggcagaggg ccgtgggctc caacgtcgcg       660
ctccgcccgc acgagaagaa gtcctacacc tacgagtggg gcaccgagat cgaccagaag       720
accaccatca tcaacaccct cggcttccag atcaacatcg acagcggcat gaagttcgac       780
atcccggagg tgggcggcgg taccgacgag atcaagaccc agctcaacga ggagctcaag       840
atcgagtact cccacgagac gaagatcatg gagaagtacc aggagcagtc cgagatcgac       900
aacccgaccg accagtccat gaactccatc ggcttcctca ccatcacctc cctggagctc       960
taccgctaca cggctccga gatccgcatc atgcagatcc agacctccga caacgacacc      1020
tacaacgtga cctcctaccc gaaccaccag caggccctgc tgctgctgac caaccactcc      1080
tacgaggagg tggaggagat caccaacatc ccgaagtcca ccctcaagaa gctcaagaag      1140
tactacttc                                                             1149
```